(12) United States Patent
Yamashita et al.

(10) Patent No.: US 7,560,236 B2
(45) Date of Patent: Jul. 14, 2009

(54) MICROBIAL COMMUNITY ANALYSIS

(75) Inventors: Yoshihisa Yamashita, Fukuoka (JP); Yoshio Nakano, Fukuoka (JP); Toru Takeshita, Fukuoka (JP)

(73) Assignee: Kao Corporation, Tokyo (JP)

( * ) Notice: Subject to any disclaimer, the term of this patent is extended or adjusted under 35 U.S.C. 154(b) by 12 days.

(21) Appl. No.: 11/759,692

(22) Filed: Jun. 7, 2007

(65) Prior Publication Data

US 2008/0305475 A1    Dec. 11, 2008

(51) Int. Cl.
*C12Q 1/68*    (2006.01)
*C12P 19/34*    (2006.01)

(52) U.S. Cl. .......................... 435/6; 435/91.1; 435/91.2

(58) Field of Classification Search ........................ None
See application file for complete search history.

(56) References Cited

U.S. PATENT DOCUMENTS

| 2006/0147976 A1 | 7/2006 | Maruyama et al. |
| 2006/0154292 A1 | 7/2006 | Maruyama et al. |

FOREIGN PATENT DOCUMENTS

| JP | 2003-265199 | 9/2003 |
| JP | 2006-25791 | 2/2006 |
| JP | 2006-42817 | 2/2006 |
| JP | 2006-94830 | 4/2006 |

OTHER PUBLICATIONS

Sakamoto et al., "Application of terminal RFLP analysis to characterize oral bacterial flora in saliva of healthy subjects and patients with periodontitis," Journal of Medical Microbiology, 2003, vol. 52, pp. 79-89.*
Moeseneder et al., Appl. Environ. Microbiol. 65(8), 3518-25 1999.
Kuske et al., Appl. Environ. Microbiol. 68(4), 1854-63 2002.
Nagashima et al., Appl. Environ. Microbiol. 69(2), 1251-62 2003.
Sakamoto et al., J. Med. Microbiol., 52, 79-89 2003.

* cited by examiner

*Primary Examiner*—Young J Kim
(74) *Attorney, Agent, or Firm*—Oblon, Spivak, McClelland, Maier & Neustadt, P.C.

(57) ABSTRACT

The present invention provides a method which can enhance the precision of identification of bacterial species using a T-RFLP method and achieve, by itself, the identification of bacteria constituting a bacterial flora and the tracing of distribution changes thereof. The present invention provides a method for analyzing a bacterial community including: amplifying DNAs extracted from a bacterial community by PCR using 16S rRNA genes as templates and fluorescently labeled primers; cleaving the amplification products with a restriction enzyme to thereby obtain sample PCR fragments; electrophoresing the sample PCR fragments together with size standard PCR fragments; and comparing the mobilities thereof to thereby determine the sizes of the sample PCR fragments, wherein PCR fragments amplified by using, as a template, a 16S rRNA gene derived from a bacterium contained in the bacterial community to be analyzed are used as the size standards.

9 Claims, 4 Drawing Sheets

MICROBIAL COMMUNITY ANALYSIS

FIELD OF THE INVENTION

The present invention relates to a method for analyzing a bacterial community using a T-RFLP method.

BACKGROUND OF THE INVENTION

For environments such as oral cavities, in which a complex bacterial flora exists, it is difficult to describe the cause of diseases or the like by merely determining the presence or absence of a certain bacterium. Thus, the establishment of analysis systems that can identify bacterial flora patterns has been deemed to be desired.

In the analysis of a bacterial flora constituted by plural microorganisms, gene analysis methods such as clone library, FISH (Fluorescent In Situ Hybridization), DGGE (Denaturing Gradient Gel Electrophoresis), and T-RFLP (Terminal Restriction Fragment Length Polymorphism) methods have been employed in recent years. Of them, since the T-RFLP method provides for high resolution or sensitivity, convenient operation, and multi-sample processing in short time, the T-RFLP method is particularly useful for the rapid analysis of samples containing unknown bacterial species or many bacterial species.

Methods for analyzing a bacterial flora on the basis of 16S rRNA gene sequences using the T-RFLP method have been utilized in many fields such as industrial or medical fields, for example, wastewater treatment, bioremediation, and slime control (JP-A-2006-94830, JP-A-2006-25791, JP-A-2006-42817, and JP-A-2003-265199; Appl. Environ. Microbiol., 65 (8), 3518-25, 1999; Appl. Environ. Microbiol., 68 (4), 1854-63, 2002; Appl. Environ. Microbiol., 69 (2), 1251-62, 2003; and J. Med. Microbiol., 52, 79-89, 2003).

In the T-RFLP method, when using bacteria with already determined 16S rRNA gene sequences, the lengths of fragments cleaved with a restriction enzyme can be calculated as theoretical values by use of Ribosome Data Project II (RD-PII), Microbial Community Analysis (MiCA), and the like. However, this method presented the problem of difficulty in assigning bacteria since the number of bases of samples measured with actual fragment-length measurement (capillary electrophoresis) deviates from the theoretical values. Thus, an approach has been adopted in many cases in which the T-RFLP method is carried out simultaneously with the clone library method and compared therewith to thereby assign bacterial species corresponding to peaks. However, this approach requires enormous cost and efforts for conducting analysis using many samples.

Moreover, bacteria accidentally having the same lengths of 5'-terminal cleaved fragments cannot be distinguished by single restriction enzyme treatment. Therefore, this method presented the problem that plural restriction enzyme treatments must be done.

SUMMARY OF THE INVENTION

The present invention relates to the following embodiments 1) to 4):

1) A method for analyzing a bacterial community including:
   amplifying DNAs extracted from a bacterial community by PCR using 16S rRNA genes as templates and fluorescently labeled primers;
   cleaving the amplification products with a restriction enzyme to thereby obtain sample PCR fragments;
   electrophoresing the sample PCR fragments together with size standard PCR fragments; and
   comparing the mobilities thereof to thereby determine the sizes of the sample PCR fragments,
   wherein PCR fragments prepared by using, as a template, a 16S rRNA gene derived from a bacterium contained in the bacterial community to be analyzed are used as the size standards.

2) A method for analyzing a bacterial community including the following steps a) to d):
   a) extracting DNAs from a bacterial community, amplifying the DNAs by PCR using 16S rRNA genes as templates and fluorescently labeled primers, and cleaving the amplification products with a restriction enzyme to thereby prepare sample PCR fragments;
   b) preparing a fluorescently labeled PCR fragment by PCR amplification using, as a template, a 16S rRNA gene derived from a bacterium contained in the bacterial community to be analyzed, and cleaving the amplification product with a restriction enzyme to thereby prepare size standard PCR fragments;
   c) simultaneously electrophoresing the size standard PCR fragments and the sample PCR fragments, and comparing the mobilities thereof to thereby determine the sizes of the sample PCR fragments with reference to the molecular weights of the size standard PCR fragments; and
   d) comparing the sizes obtained at the step c) with sizes in a database to thereby identify bacterial species.

3) A method for analyzing an oral bacterial flora including:
   amplifying DNAs extracted from an oral bacterial community by PCR using 16S rRNA genes as templates and fluorescently labeled primers;
   cleaving the amplification products with a restriction enzyme to thereby obtain sample PCR fragments;
   electrophoresing the sample PCR fragments together with size standard PCR fragments; and
   comparing the mobilities thereof to thereby determine the sizes of the sample PCR fragments,
   wherein PCR fragments prepared by using, as a template, a 16S rRNA gene derived from an oral bacterium are used as the size standards.

4) A method for analyzing an oral bacterial flora including the following steps a) to d):
   a) extracting DNAs from an oral bacterial community, amplifying the DNAs by PCR using 16S rRNA genes as templates and fluorescently labeled primers, and cleaving the amplification products with a restriction enzyme to thereby prepare sample PCR fragments;
   b) preparing a fluorescently labeled PCR fragment by PCR amplification using, as a template, a 16S rRNA gene derived from an oral bacterium, and cleaving the amplification product with a restriction enzyme to thereby prepare size standard PCR fragments;
   c) simultaneously electrophoresing the size standard PCR fragments and the sample PCR fragments, and comparing the mobilities thereof to thereby determine the sizes of the sample PCR fragments with reference to the molecular weights of the size standard PCR fragments; and
   d) comparing the sizes obtained at the step c) with sizes in a database to thereby identify bacterial species.

DETAILED DESCRIPTION OF THE PREFERRED EMBODIMENTS

Figure 1A:
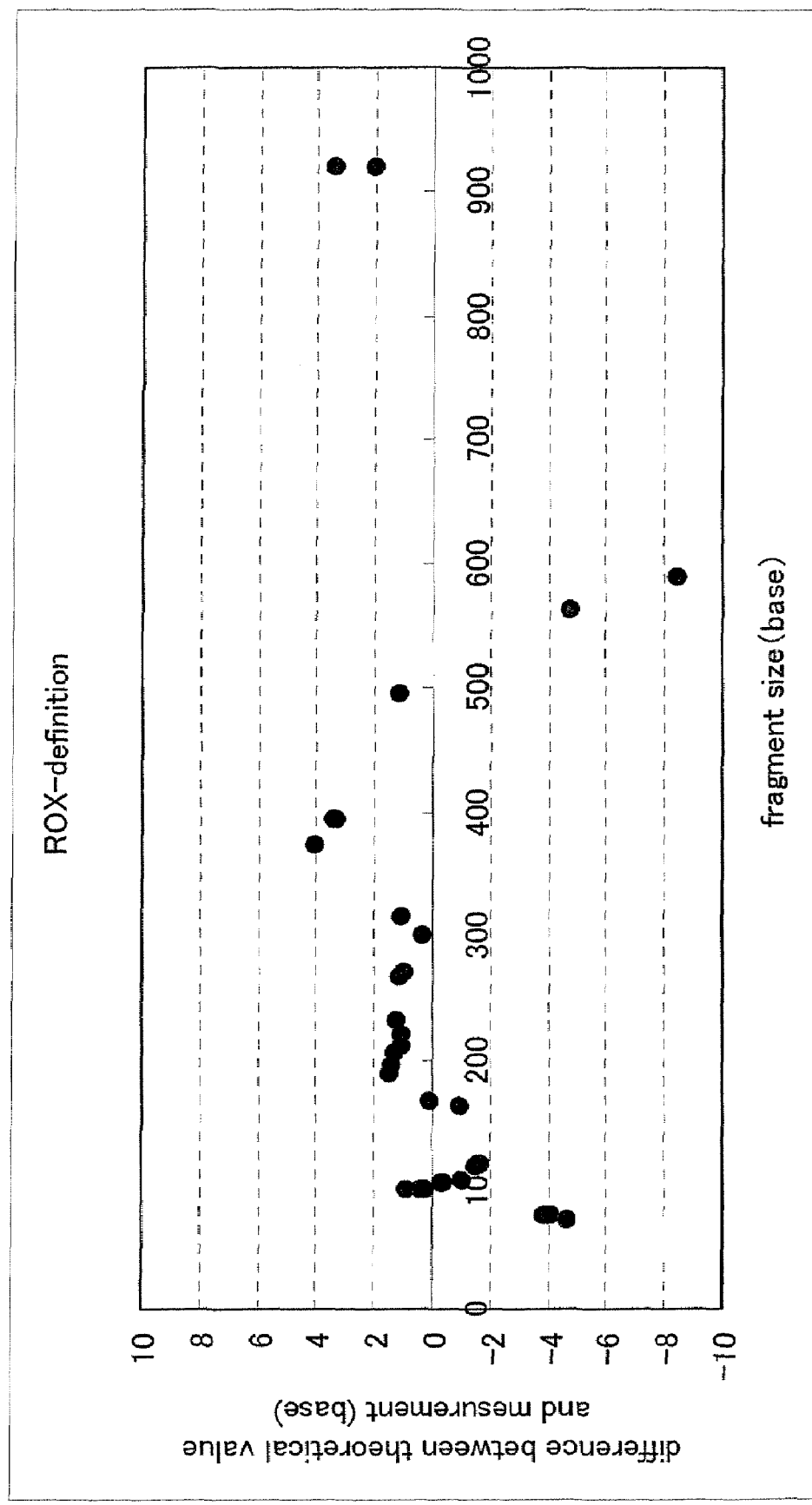
FIG. 1 shows the comparison in deviation correction effect between the use of commercially available size standards (ROX-definition, upper diagram) and the use of size standards based on 16S rRNA sequences (FAM-definition, lower diagram)

The present invention provides a method which can enhance the precision of identification of bacterial species using a T-RFLP method and achieve, by itself, the identification of bacteria constituting a bacterial flora and the tracing of distribution changes thereof.

The present inventors have studied for achieving, in bacterial flora analysis using a T-RFLP method, reduction in error occurring between fragment lengths obtained by electrophoresis and fragment lengths predicted from the sequences and have consequently found that PCR fragments prepared by using, as a template, a 16S rRNA gene derived from a bacterium contained in a bacterial flora to be analyzed can be used as size standards to thereby reduce the error.

A method of the present invention can achieve, by itself, the identification of bacteria constituting a bacterial flora and the tracing of distribution changes thereof without using a clone library method or the like. Thus, the method of the present invention is useful as an exhaustive analysis method for an oral flora, for example.

Hereinafter, the method for analyzing a bacterial community of the present invention will be described with reference to each step.

1) DNA Extraction

DNA mixtures are collected from a sample to be analyzed.

The sample used herein may be a sample containing complex microorganism groups, though differing according to an analyte, and encompasses all microorganism-containing samples from natural environments or in-vivo environments. For example, saliva, dental plaques, or fur coatings of tongue are used in oral bacterial flora analysis, while feces or biopsies are used in intestinal bacterial flora analysis.

DNAs can be collected from a sample by a known method and may be extracted by use of, for example, bead shaking, bacterial homogenization with an enzyme or a commercially available kit, and purified appropriately.

2) 16S rRNA Gene Amplification

The extracted DNAs are subjected to the PCR amplification of 16S rRNA genes used as indicator sequences by using fluorescently labeled primers. The 16S rRNA genes (16S rDNAs) are generally utilized as molecular biological classification indicators for microorganisms and are the most preferable indicator sequences in the bacterial community analysis of the present invention.

The primers used are those suitable for the amplification of 16S rRNA genes and have to be designed so that amplified regions contain all 16S rRNA gene copies. For oral bacterial flora analysis, primers shown in Examples below, for example, 8F, 806R, D88, and E94 are preferably utilized.

Such primers used include two primers, upstream and downstream primers, either or both of which is preferably labeled at the 5' or 3' end with a fluorescent dye. Amplification in forward and reverse directions is preferable using a 5'-terminal primer (forward primer) fluorescently labeled with a certain color and a 3'-terminal primer (reverse primer) fluorescently labeled with a color different from the above color.

The use of such a primer set can double information obtained from single restriction enzyme treatment and can halve the work. Moreover, it can improve the precision of identification of bacteria and quantitative properties.

Any fluorescent dye known in the art can be utilized as the fluorescent dye for use in such fluorescent labeling. Among others, for example, FAM (6-Carboxyfluorescein), HEX (6-carboxy-2',4,4',5',7,7'-hexachlorofluorescein), ROX (5(6)-Carboxy-X-rhodamine), JOE (6-carboxy-4',5'-dichloro-2',7'-dimethoxyfluorescein), TET (5'-tetrachlorofluorescein phosphoramidite), NED (fluorescein benzoxanthene), TAMRA (6-carboxy-N,N,N,N-tetramethylrhodamine), FITC (fluorescein isothiocyanate), VIC, PET, Texas Red, Cy3, and Cy5 are preferable, and FAM, HEX, and ROX are more preferable, in light of photostability, wavelength regions, versatility, and so on.

The fluorescently labeled primers used in the present invention are particularly preferably a set of a forward primer labeled at the 5' end with FAM and a reverse primer labeled at the 3' end with HEX.

The PCR amplification can be achieved through, for example, approximately 30 cycles each consisting of denaturation (98° C., 15 sec.), annealing (60° C., 2 sec.), and elongation (72° C., 30 sec.)

3) Cleavage of Amplified PCR Products with Restriction Enzyme

The amplified PCR products are cleaved with an appropriate restriction enzyme after removing the residual primers.

The restriction enzyme that can be used is any of those known in the art and include AciI, TaqI, HhaI, AluI, MseI, SacII, BstUI, RsaI, HaeIII, MspI, CfoI, MrnI, San96I, FokI, AlnI, DdeI, HinfI, and MboI. These restriction enzymes can be used alone or in combination of two or more of them.

4) Determination of Sizes of Cleaved Sample PCR Fragments a) Size Standard PCR Fragments:

A fluorescently labeled PCR fragment derived from the same fluorescently labeled primers as above is amplified by using, as a template, a 16S rRNA gene derived from a bacterium contained in the bacterial community to be analyzed. The amplification product is cleaved with the restriction enzyme described above to thereby prepare size standard PCR fragments.

Size standards conventionally used in the T-RFLP method are those having no nucleotide sequence common to 16S rRNA genes, for example, GeneScan 500-ROX (Applied Biosystems), which is an enzyme-digested plasmid fragment. However, the use of, as size standards, the fragments of a 16S rRNA gene derived from a bacterium contained in the bacterial community to be analyzed can reduce errors probably derived from fragment conformation.

The 16S rRNA gene derived from a bacterium is preferably any of those derived from bacteria contained in the bacterial community to be analyzed which having an average 16S rRNA gene sequence. For example, a 16S rRNA gene from an oral bacterium such as *Porphyromonas gingivalis* is preferably used for oral bacterial flora analysis.

In the analysis method of the present invention, for example, commercially available Genescan-500ROX may be used actually as the size standard PCR fragments by preparing an additional database from the comparison between the mobility of the size standard PCR fragments of the present invention (e.g., FAM-labeled size standards or HEX-labeled size standards) and the mobility of the Genescan-500ROX.

b) Determination of Sizes of Sample PCR Fragments

The size standard PCR fragments and the sample PCR fragments are simultaneously electrophoresed, and the mobilities thereof are compared between them to thereby determine the sizes of the sample PCR fragments.

The electrophoresis of the sample PCR fragments together with the size standard PCR fragments can be carried out by use of a capillary electrophoresis apparatus or the like. Detection is conducted on the basis of the fluorescence of the labels.

Subsequently, the electrophoretic mobilities thereof are compared to thereby determine the sizes of the sample PCR fragments. In this procedure, the sizes of the sample PCR fragments are preferably determined with reference to the molecular weights of the size standard PCR fragments.

DNA fragment lengths have conventionally been defined by the number of bases (bases). However, the deviation thereof from theoretical values can be reduced effectively by indicating the DNA fragment lengths in molecular weight (MW) rather than in the number of bases, as shown in Examples below. Thus, the fragment lengths can be measured more accurately.

The size standard length can be indicated on a molecular weight basis according to the following numerical formula:

Molecular Weight=($NA$×313.2)+($NC$×289.2)+($NG$×329.2)+($NT$×304.2)−61.9+fluorescent dye molecular weight, wherein NA, NC, NG, and NT denote the numbers of bases A, C, G, T, respectively.

5) Identification of Bacterial Species

Actual bacterial flora analysis can be conducted by use of analysis software (Genemapper 4.0, ABI), wherein bacterial species can be identified by applying information such as the obtained fragment molecular weights and the restriction enzyme species used to the 16S rRNA gene database TRF-MAW.

EXAMPLE 1

Advantage of Use of Size Standard from 16S rRNA Gene Sequence

<DNA Extraction from Standard Bacterium>

Seven bacterial species, *Streptococcus mutans* (Sm), *Veillonella parvula* (Vp), *Neisseria mucosa* (Nm), *Fusobacterium nucleatum* (Fn), *Rothia dentocariosa* (Rd), *Porphyromonas endodontalis* (Pe), and *Porphyromonas gingivalis* (Pg), were cultured according to a standard method. The centrifugation pellet fractions thereof were subjected to subsequent study. Each bacterial chromosomal DNA was prepared by use of IsoQuick (Orca Research, WA).

<Preparation of Size Standard Specific to 16S rRNA Gene>

The chromosomal DNA of a *Porphyromonas gingivalis* W83 strain was prepared by use of IsoQuick. This DNA was used as a template to thereby prepare FAM-labeled size standards. A DNA fragment contained in each standard is shown below.

(i) FAM-Labeled Size Standard (Base Length of Fluorescently Labeled Fragment Contained in Solution)

1) D88-FAM primer (21 bases)
2) PCR product derived from D88-FAM and 806R and treated with TaqI (56 bases)
3) PCR product derived from D88-FAM and 806R and treated with AluI (77 bases)
4) PCR product derived from D88-FAM and 806R and treated with HhaI (103 bases)
5) PCR product derived from D88-FAM and 806R and treated with AciI (172 bases)
6) PCR product derived from D88-FAM and 237m (237 bases)
7) PCR product derived from D88-FAM and 295m (295 bases)
8) PCR product derived from D88-FAM and 361m (361 bases)
9) PCR product derived from D88-FAM and 414m (414 bases)
10) PCR product derived from D88-FAM and 475m (475 bases)
11) PCR product derived from D88-FAM and 542m (542 bases)
12) PCR product derived from D88-FAM and 601m (601 bases)
13) PCR product derived from D88-FAM and 664m (664 bases)
14) PCR product derived from D88-FAM and 731m (731 bases)
15) PCR product derived from D88-FAM and 806R (800 bases)
16) PCR product derived from D88-FAM and 861m (861 bases)
17) PCR product derived from D88-FAM and F17 (919 bases)
18) PCR product derived from D88-FAM and 977m (977 bases)

<Primer Sequence 5'-( )-3'>

| | |
|---|---|
| D88>GAGAGTTTGATYCTGGCTCAG | (SEQ ID NO: 1) |
| D88-FAM><br>[6FAM] -GAGAGTTTGATYCTGGCTCAG | ([6FAM]-<br>SEQ ID NO: 1) |
| E94>GAAGGAGGTGWTCCARCCGCA | (SEQ ID NO: 2) |
| 237m>CGCATGCCTATCTTACAGCT | (SEQ ID NO: 3) |
| 295m>AGTTCCCCTACCCATCGTCG | (SEQ ID NO: 4) |
| 361m>CCTCACTGCTGCCTCCCGTA | (SEQ ID NO: 5) |
| 421m>TAGGACTGTCTTCCTTCACG | (SEQ ID NO: 6) |
| 484m>CGGTACATTCAATGCAATAC | (SEQ ID NO: 7) |
| 542m>CTCGCATCCTCCGTATTACC | (SEQ ID NO: 8) |
| 601m>TCACCGCTGACTTACCGAAC | (SEQ ID NO: 9) |
| 664m>CTGCCGCCACTGAACTCAAG | (SEQ ID NO: 10) |
| 731m>AAGCTGCCTTCGCAATCGGA | (SEQ ID NO: 11) |
| 861m>GCTTTCGCTGTGGAAGCTTG | (SEQ ID NO: 12) |
| F17>CCGTCWATTCMTTTGAGTTT | (SEQ ID NO: 13) |
| 976m>GTAAGGTTCCTCGCGTATCA | (SEQ ID NO: 14) |

PCR reaction was carried out on a scale of 50 µl in total volume comprising 5 µl of DNA extract, 5 U of KOD polymerase (TOYOBO), dNTP added at a final concentration of 250 µM, MgCl$_2$ added at a final concentration of 1 mM, and each primer added at a final concentration of 1 µM. After 30 cycles of PCR reaction (denaturation: 98° C., 15 sec., annealing: 60° C., 2 sec., and elongation: 72° C., 30 sec.), the resulting products were purified by use of a QIAEX II gel extraction kit (Qiagen, Germany). Restriction enzyme reaction was carried out by digesting the FAM-labeled DNA fractions thus prepared with restriction enzymes at their respective appropriate temperatures for 2 hours, followed by inactivation at high temperatures. The primers used were diluted to 0.1 pmol/µl. These solutions were mixed at equal DNA concentrations to thereby prepare FAM-labeled size standards.

<Redefinition of Base Number of Length of Commercially Available Size Standard>

To 1 µl of GeneScan 1000-ROX (Applied Biosystems), 2 µl of FAM-labeled size standard and 10 µl of formamide were added. The mixture was applied to a DNA sequencer ABI3130 (Applied Biosystems) to thereby separate and detect each fragment. The number of bases of each GeneScan 1000-ROX fragment was redefined as those with reference to the FAM-labeled size standards by comparing the mobilities thereof with those of the FAM-labeled size standards.

<PCR Amplification of Sample>

The bacterial 16S rRNA gene sequences were amplified by PCR using the following primers:

```
                                    ([6FAM]]- SEQ ID NO: 1)
Forward:
D88-FAM    5' [6FAM] - (GAGAGTTTGATYCTGGCTCAG) -3'

(SEQ ID NO: 2)
Reverse:
E94        5' - (GAAGGAGGTGWTCCARCCGCA)-3'
```

PCR reaction was carried out on a scale of 50 µl in total volume containing 5 µl of DNA extract, 5 U of Ex Taq polymerase (Takara Bio), dNTP added at a final concentration of 250 µM, and each primer added at a final concentration of 1 µM. After 30 cycles of PCR reaction, each 1 µl aliquot of the resulting PCR products was subjected to 0.8% agarose gel electrophoresis and subsequent DNA fraction purification using a Wizard SV Gel and PCR clean up system (Promega, Madison, Wis.).

<T-RFLP Analysis>

Each 3 µl aliquot of the purified DNA fractions was digested with 2.5 U of an arbitrary restriction enzyme (e.g., HhaI, AluI, or HaeIII) on a scale of 10 µl in total volume. To 2 µl of the digested fragment, 0.5 µl of GeneScan 1000-ROX and 10 µl of formamide were added. The mixture was subjected to DNA denaturation reaction to thereby convert the fluorescently labeled fragments into single strands, which were then applied to a DNA sequencer ABI3130 (Applied Biosystems) to thereby separate and detect each fragment. The lengths (the number of bases) of the detected FAM-labeled fragments derived from the samples were calculated and converted by comparing the mobilities thereof with those of the GeneScan 1000-ROX redefined by each size standard. Actual bacterial flora analysis was conducted by use of analysis software (Genemapper 4.0, ABI) and TRFMA (Nakano Y. et al.: Bioinformatics 2006, 22, 1788-1789).

<Result>

Figure 1B:
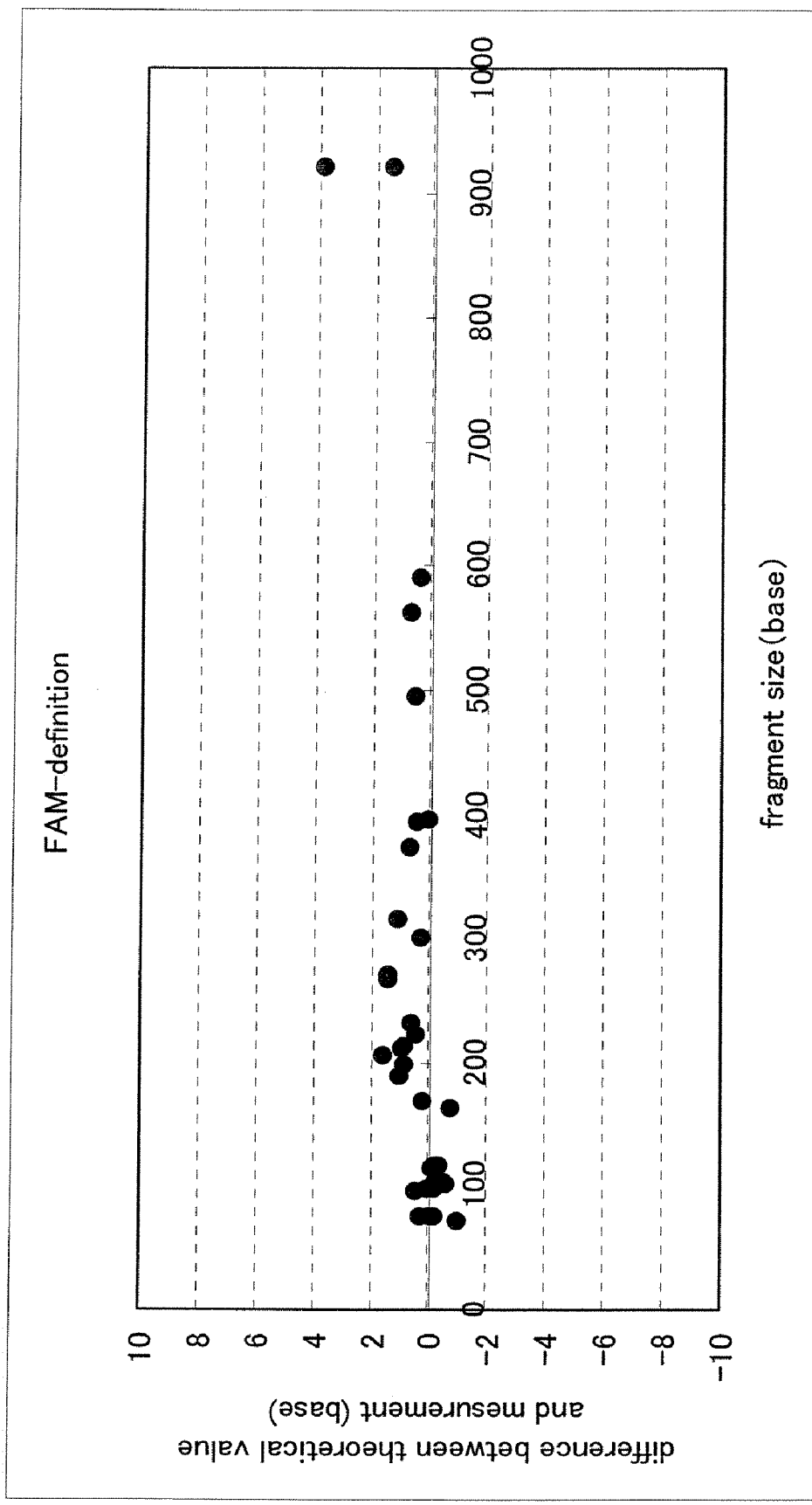

Deviation from the theoretical value (error) for each bacterium-derived fragment length was compared between the data obtained from the direct use of the commercially available size standard as a fragment length indicator (ROX-definition, conventional method) and those from the fragment length redefinition using 16S rRNA gene fragments (FAM-definition). As a result, the error was significantly reduced in the FAM-definition (FIG. 1).

EXAMPLE 2

Advantage of Combined Use of Size Standard Modification, Determination on Molecular Weight Basis and Dichromatic Method <DNA Extraction from Standard Bacteria and Biological Sample>

Five bacterial species, *Streptococcus mutans* (*Sm*), *Veillonella parvula* (*Vp*), *Neisseria mucosa* (*Nm*), *Fusobacterium nucleatum* (*Fn*), and *Rothia dentocariosa* (*Rd*), were cultured according to a standard method. The centrifugation pellet fractions thereof were subjected to subsequent study. Each bacterial chromosomal DNA was prepared by use of IsoQuick. Pellets obtained by the centrifugation (15,000 rpm, 15 min., 4° C.) of 0.5 ml of human saliva were used as an oral bacterial fraction. The pellets were suspended in 150 µl of dispersing solution (50 mM Tris-HCl buffer (pH 7.6), 1 mM EDTA, and 1% SDS). After the addition of 0.3 g of zirconia-silica beads (0.1 mm φ, Biospec Products, OK), the mixture was heated (90° C., 10 min.) and homogenized by shaking using a Disruptor Genie cell disrupter (3 min., Scientific Industries, NY). The homogenate solution was centrifuged, and the resulting supernatant was then supplemented with 200 µl of 1% SDS and heated (70° C., 10 min.), followed by extraction with 400 µl of extracting solution (phenol-chloroform-isoamyl alcohol (25:24:1)) and precipitation with 100% ethanol to thereby obtain a crude DNA fraction. The fraction was further washed with 70% ethanol, then resuspended in 100 µl of TE buffer, and cryopreserved.

<Preparation of Size Standard Specific to 16S rRNA Gene>

The chromosomal DNA of a *Porphyromonas gingivalis* W83 strain was prepared by use of IsoQuick. This DNA was used as a template to thereby prepare two groups of size standards, FAM- and HEX-labeled size standards. A DNA fragment contained in each standard is shown below.

(i) FAM-Labeled Size Standard (Base Length of Fluorescently Labeled Fragment Contained in Solution)

1) 8F-FAM primer (20 bases)
  2) PCR product derived from 8F-FAM and 806R and treated with TaqI (55 bases)
  3) PCR product derived from 8F-FAM and 806R and treated with AluI (76 bases)
  4) PCR product derived from 8F-FAM and 806R and treated with HhaI (102 bases)
  5) PCR product derived from 8F-FAM and 806R and treated with AciI (171 bases)
  6) PCR product derived from 8F-FAM and 237m (236 bases)
  7) PCR product derived from 8F-FAM and 295m (294 bases)
  8) PCR product derived from 8F-FAM and 361m (360 bases)
  9) PCR product derived from 8F-FAM and 414m (413 bases)
  10) PCR product derived from 8F-FAM and 475m (474 bases)
  11) PCR product derived from 8F-FAM and 542m (541 bases)
  12) PCR product derived from 8F-FAM and 601m (600 bases)

13) PCR product derived from 8F-FAM and 664m (663 bases)
14) PCR product derived from 8F-FAM and 731m (730 bases)
15) PCR product derived from 8F-FAM and 806R (799 bases)
16) PCR product derived from 8F-FAM and 861m (860 bases)
17) PCR product derived from 8F-FAM and F17 (918 bases)
18) PCR product derived from 8F-FAM and 977m (976 bases)

(ii) HEX-Labeled Size Standard (Base Length of Fluorescently Labeled Fragment Contained in Solution)
1) 806R-HEX primer (19 bases)
2) PCR product derived from 806R-HEX and 8F and treated with AluI (72 bases)
3) PCR product derived from 806R-HEX and 8F and treated with AciI (116 bases)
4) PCR product derived from 806R-HEX and 8F and treated with HhaI (191 bases)
5) PCR product derived from 806R-HEX and 8F and treated with MseI (234 bases)
6) PCR product derived from 806R-HEX and 8F and treated with SacII (280 bases)
7) PCR product derived from 806R-HEX and r354m (354 bases)
8) PCR product derived form 806R-HEX and r430m (430 bases)
9) PCR product derived from 806R-HEX and r489m (489 bases)
10) PCR product derived from 806R-HEX and r563m (563 bases)
11) PCR product derived from 806R-HEX and r640m (640 bases)
12) PCR product derived from 806R-HEX and r725m (725 bases)
13) PCR product derived from 806R-HEX and 8F (799 bases)
14) PCR product derived from 806R-HEX and R948m (948 bases)

<Primer Sequence 5'-( )-3'>

```
8F>AGAGTTTGATYMTGGCTCAG'            (SEQ ID NO: 15)

8F-FAM>                              ([6FAM] -
[6FAM] -AGAGTTTGATYMTGGCTCAG         SEQ ID NO: 15)

806R>GGACTACCRGGGTATCTAA             (SEQ ID NO: 16)

806R-HEX>GGACTACCRGGGTATCTAA'        ([5HEX] -
                                     SEQ ID NO: 16)

237m>CGCATGCCTATCTTACAGCT            (SEQ ID NO: 3)

295m>AGTTCCCCTACCCATCGTCG            (SEQ ID NO: 4)

361m>CCTCACTGCTGCCTCCCGTA            (SEQ ID NO: 5)

421m>TAGGACTGTCTTCCTTCACG            (SEQ ID NO: 6)

484m>CGGTACATTCAATGCAATAC            (SEQ ID NO: 7)

542m>CTCGCATCCTCCGTATTACC            (SEQ ID NO: 8)

601m>TCACCGCTGACTTACCGAAC            (SEQ ID NO: 9)

664m>CTGCCGCCACTGAACTCAAG            (SEQ ID NO: 10)

731m>AAGCTGCCTTCGCAATCGGA            (SEQ ID NO: 11)

861m>GCTTTCGCTGTGGAAGCTTG            (SEQ ID NO: 12)

F17>CCGTCWATTCMTTTGAGTTT             (SEQ ID NO: 13)

976m>GTAAGGTTCCTCGCGTATCA            (SEQ ID NO: 17)

r354m>GAATAACGGGCGATACGAG            (SEQ ID NO: 18)

r430m>CAATGGGCGAGAGCCTGAA            (SEQ ID NO: 19)

r489m>ACACTGGTACTGAGACACG            (SEQ ID NO: 20)

r563m>TCCCATTAGCTTGTTGGTG            (SEQ ID NO: 21)

r640m>ACGGACTAAAACCGCATAC            (SEQ ID NO: 22)

r725m>AGCTTGCTAAGGTTGATGG            (SEQ ID NO: 23)

r948m> TCTTTGACAGAGTATATGTC          (SEQ ID NO: 24)
```

PCR reaction was carried out on a scale of 50 μl in total volume containing 5 μl of DNA extract, 5 U of KOD polymerase (TOYOBO), dNTP added at a final concentration of 250 μM, $MgCl_2$ added at a final concentration of 1 mM, and each primer added at a final concentration of 1 μM. After 30 cycles of PCR reaction (denaturation: 98° C., 15 sec., annealing: 60° C., 2 sec., and elongation: 72° C., 30 sec.), the resulting products were purified by use of a QIAEX II gel extraction kit (Qiagen, Germany).

Restriction enzyme reaction was carried out by digesting the FAM- and HEX-labeled DNA fractions thus prepared with restriction enzymes at their respective appropriate temperatures for 2 hours, followed by inactivation at high temperatures. The primers used were diluted to 0.1 pmol/μl. These solutions were mixed at equal DNA concentrations to respectively prepare FAM- and HEX-labeled size standards.

<Indication of Length of Commercially Available Size Standard on Molecular Weight Basis>

Four ROX-labeled DNA fragments (600, 730, 860, and 918 bases) were newly added to GeneScan 500-ROX (Applied Biosystems) to thereby prepare modified GeneScan 500-ROX. To 1 μl of modified GeneScan 500-ROX, 2 μl of FAM- or HEX-labeled size standard and 10 μl of formamide were added. The mixture was applied to a DNA sequencer ABI3130 (Applied Biosystems) to thereby separate and detect each fragment. The molecular weight of each fragment of modified GeneScan 500-ROX was calculated by comparing the mobilities thereof with those of the FAM- or HEX-labeled size standards of known molecular weights. The fragment lengths on the base number basis (bases) were redefined to be indicated on a molecular weight (MW) basis.

<PCR Amplification of Sample>

The bacterial 16S rRNA gene sequences were amplified by PCR using the following primers:

```
                                    ([6FAM] -SEQ ID NO: 15)
Forward:
8F-FAM   5' [6FAM] - (AGAGTTTGATYMTGGCTCAG) -3'

([5HEX] -SEQ ID NO: 16)
Reverse:
806R-HEX 5' [5HEX] - (GGACTACCRGGGTATCTAA) -3'
```

PCR reaction was carried out on a scale of 50 μl in total volume comprising 5 μl of DNA extract, 5 U of KOD polymerase (TOYOBO), dNTP added at a final concentration of 250 μM, and each primer added at a final concentration of 1

μM. After 30 cycles of PCR reaction, each 1 μl aliquot of the resulting PCR products was subjected to 0.8% agarose gel electrophoresis and subsequent DNA fraction purification using a Wizard SV Gel and PCR clean up system (Promega, Madison, Wis.).

<T-RFLP Analysis>

Each 3 μl aliquot of the purified DNA fractions was digested with 2.5 U of an arbitrary restriction enzyme (e.g., HhaI, AluI, or HaeIII) on a scale of 10 μl in total volume. To 2 μl of the digested fragment, 0.5 μl of modified GeneScan 500-ROX and 10 μl of formamide were added. The mixture was subjected to DNA denaturation reaction to thereby convert the fluorescently labeled fragments into single strands, which were then applied to a DNA sequencer ABI3130 (Applied Biosystems) to thereby separate and detect each fragment. The molecular weights of the detected FAM- or HEX-labeled fragments derived from the samples were calculated and converted by comparing the mobilities thereof with those of the modified GeneScan 500-ROX redefined by each size standard. Actual bacterial flora analysis was conducted by use of analysis software (Genemapper 4.0, ABI) and TRFMA.

<Result>

Figure 2:
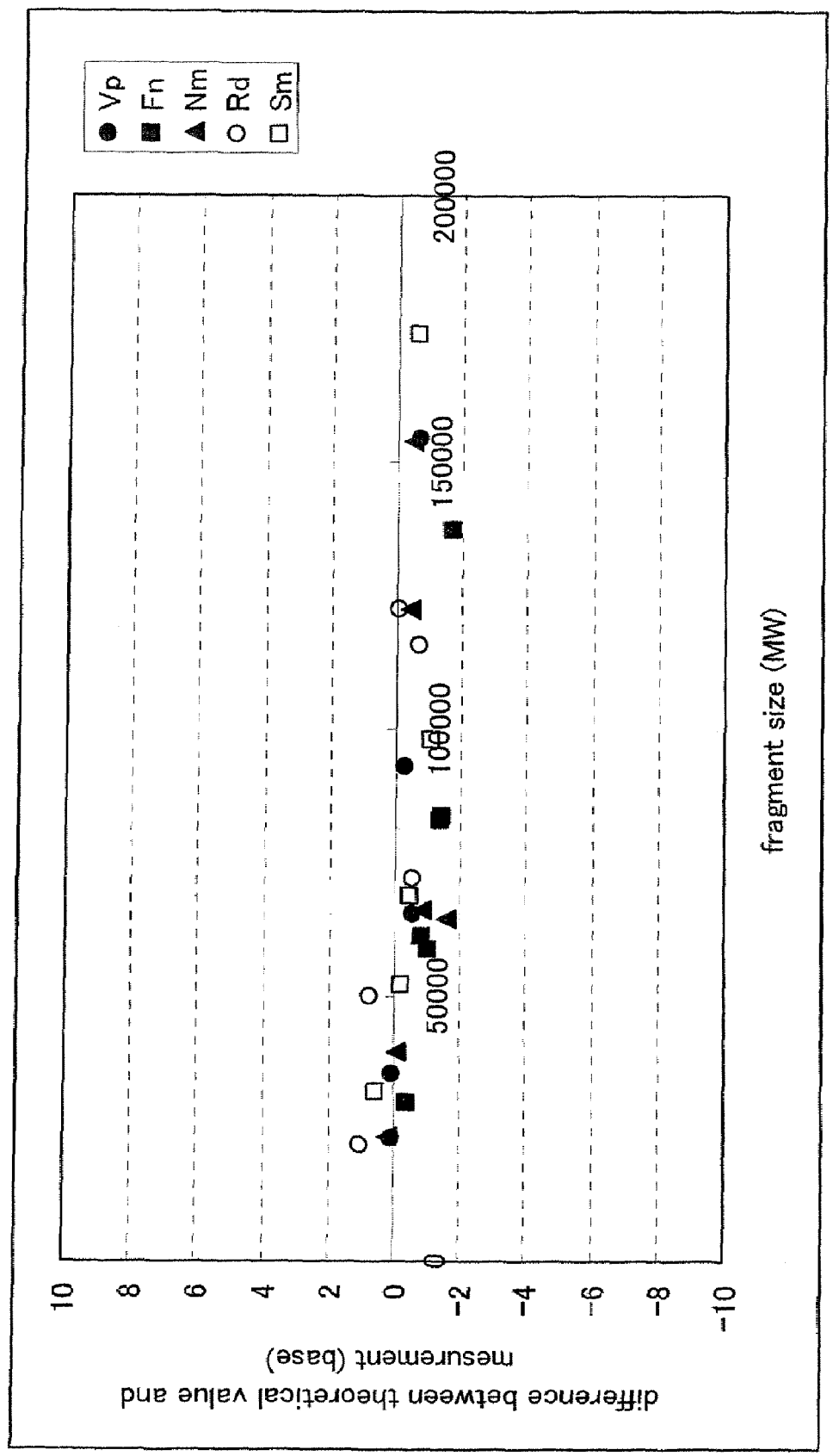
FIG. 2 shows deviation correction effect obtained by using size standards based on 16S rRNA sequences and also using the determination of fragment lengths on a molecular weight basis.

When fragment lengths were redefined by use of 16S rRNA gene fragments and converted from a base number basis to a molecular weight basis, deviation from the theoretical value for each bacterium-derived fragment length is reduced to within 2.6 bases (FIG. 2).

Figure 3:
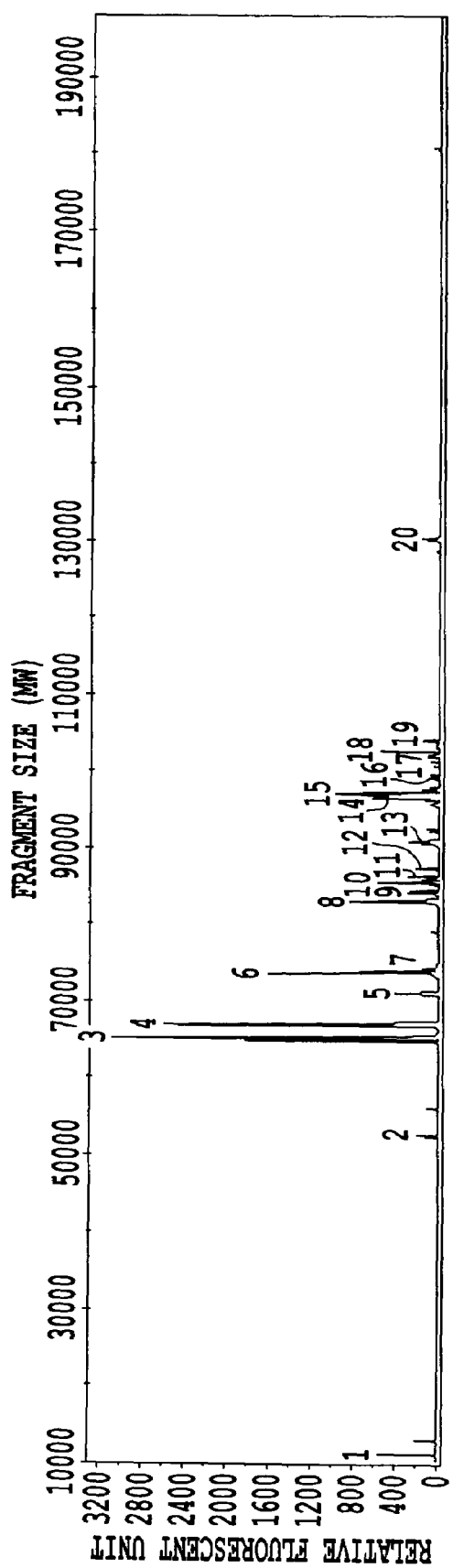
FIG. 3 shows a T-RFLP chart for human saliva.

Moreover, results of analysis using this method using human saliva as a sample was consistent with those obtained by a clone library method, demonstrating that the present method can conveniently and rapidly determine a bacterial flora (FIG. 3 and Table 1).

TABLE 1

Comparison in analysis of human saliva bacterial flora between T-RFLP method and clone library method

| peak No. | Bacterial species identified by clone library (CL) method | Bacterial species predicted by T-RFLP method (those matching the result of the CL method are indicated in bold type) |
|---|---|---|
| ① | | *Prevotella* sp. oral clone IDR-CEC-0032; _AY550995 |
| ② | *Prevotella pallens*; 9423; Y13106 | *Prevotella intermedia* |
| | | *Prevotella intermedia*; _ChDC_KB53; _AY689226 |
| | | Prevotella pallens, _9423; _Y13106 |
| ③ | *Neisseria subflava* U37; AJ239291 | *Burkholderia* sp. oral clone AK168; _AY005032 |
| | *Neisseria* sp. R-22841; AJ786809 | Neisseria subflava, _U37; _AJ239291 |
| | Uncultured bacterium clone Y167; AY975728 | Neisseria sp._R-22841; _AJ786809 |
| | *Terrahaemophilus aromaticivorans*; 127W; AB098612 | uncultured bacterium; _Y167; _AY975728 |
| | | *Haemophilus* sp._oral_clone_BJ021; _AY005034 |
| | | Terrahaemophilus aromaticivorans, _127W; _AB098612 |
| ④ | *Veillonella* sp. clone SC004B06; AY807839 | *Veillonella* sp. oral clone AA050; _AF287782 |
| | | *Veillonella* sp. oral clone X042; _AF287781 |
| | | uncultured Veillonella sp._SC004B06; _AY807839 |
| ⑥ | | *Rothia dentocariosa* |
| ⑧ | *Prevotella melaninogenica*; ATCC 25845; L16469 | *Streptococcus mitis*_(T) |
| | | *Prevotella* sp. oral clone GI032; _AY349396 |
| | | *Prevotella* sp. oral clone AO009; _AY005059 |
| | | Prevotella melaninogenica(T); _L16469 |
| | | *Prevotella* sp. oral clone BE073; _AF385551 |
| | | *Prevotella* sp. oral clone P4PB 83 P2; _AY207050 |
| | | *Prevotella* sp. oral clone DO027; _AF385511 |
| | | *Prevotella* sp. oral clone GI059; _AY349397 |
| | | *Prevotella* sp. oral clone FM005; _AF432133 |
| | | *Prevotella* sp. oral clone FU048; _AY349393 |
| | | *Prevotella* sp. oral clone HB034; _DQ087190 |
| | | *Prevotella* sp. oral clone AA020; _AY005057 |
| ⑨ | *Gemella sanguinis* 2045-94; Y13364 | *Gemella haemolysans* (T); _L14326 |
| | | *Gemella* sp. oral strain C24KA; _AY005051 |
| | | Gemella sanguinis(T); _2045-94; _Y13364 |
| ⑩ | *Fusobacterium periodonticum*; KP-F10; AJ810271 | *Fusobacterium* sp. oral clone BS011; _AF432130 |
| | | *Fusobacterium* sp. oral clone EX162; _AY134900 |
| | | *Fusobacterium* sp. OMZ 982; _AJ810274 |
| | | Fusobacterium periodonticum, _KP-F10 |
| | | *Fusobacterium nucleatum* subsp. *polymorphum*; _OMZ_76 |
| | | *Streptococcus anginosus*; _ChDC_YA9; _AY691539 |
| | | *Streptococcus anginosus*; _ChDC_YA6; _AY691537 |
| ⑪ | *Streptococcus* sp. oral strain H3-M2; AF385523 | Streptococcus sp. oral strain H3-M2; _AF385523 |
| ⑫ | *Streptococcus* sp. oral clone BM035; AY005043 | Streptococcus sp. oral clone BM035; _AY005043 |
| | *Streptococcus oralis*; ATCC 700233; AY281080 | Streptococcus oralis, _ATCC_700233; _AY281080 |
| | *Streptococcus* sp. oral clone P2PA_41 P2; AY207051 | *Streptococcus* sp. oral clone AY020; _AF385545 |
| | *Streptococcus* sp. oral clone BW009; AY005042 | *Streptococcus* sp. oral strain B5SC; _AY005047 |
| | | *Streptococcus mitis*; _ATCC_6249; _AY281077 |
| | | *Streptococcus* sp. oral clone CH016; _AY005044 |
| | | Streptococcus sp. oral clone P2PA 41 P2; _AY207051 |
| | | Streptococcus sp. oral clone BW009; _AY005042 |
| | | *Streptococcus mitis*; _mother_C3; _4C3; _AM157420 |
| | | *Streptococcus mitis* |
| | | *Streptococcus oralis*; _ATCC_9811; _AY281079 |
| | | *Streptococcus sanguinis*; _ATCC_49296; _AY281086 |
| | | *Streptococcus mitis* bv2; _SK34; _AY005045 |

TABLE 1-continued

Comparison in analysis of human saliva bacterial flora between T-RFLP method and clone library method

| peak No. | Bacterial species identified by clone library (CL) method | Bacterial species predicted by T-RFLP method (those matching the result of the CL method are indicated in bold type) |
|---|---|---|
| ⑲ | *Streptococcus salivarius* (T); ATCC 7073; AY188352<br>*Streptococcus* sp. oral strain T1-E5; AF385525<br>*Streptococcus parasanguinis* GIFU7994; AB006124<br>*Streptococcus* sp. oral strain T4-E3; AF385526<br>*Streptococcus* sp. oral clone DP009; AF432132<br>*Streptococcus* sp. oral clone P4PA_13 P3; AY207062<br>Uncultured bacterium clone NS03; AY981757 | *Streptococcus* sp. oral clone BE024; __AF385550<br>*Streptococcus mitis*<br>*Streptococcus sanguinis*; __ChDC__B203; __AF543281<br>*Streptococcus* sp. oral clone FN042; __AF432134<br>*Streptococcus* sp. oral clone EK048; __AF385574<br>Streptococcus salivarius(T); __ATCC__7073; __AY188352<br>*Streptococcus salivarius*; __AF459433<br>*Streptococcus sanguinis*<br>*Streptococcus* sp. oral clone MCE7 144; __AF481230<br>Streptococcus sp. oral strain T1-E5; __AF385525<br>Streptococcus parasanguinis<br>Streptococcus sp. oral strain T4-E3; __AF385526<br>*Streptococcus* sp. oral clone FO042; __AF432136<br>*Streptococcus* sp. oral clone FN051; __AF432135<br>Streptococcus sp. oral clone DP009; __AF432132<br>*Streptococcus* sp. oral clone DN025; __AF432131<br>Streptococcus sp. oral clone P4PA 13 P3; __AY207062<br>*Streptococcus* sp. oral strain 7A; __AY005040<br>*Streptococcus* sp. oral clone AG008; __AY134909<br>*Streptococcus* sp. oral clone AA007; __AY005046<br>*Streptococcus salivarius*; __mother__V5; __1V5; __AM157451<br>uncultured bacterium; __NS03; __AY981757<br>*Streptococcus* sp. oral clone FP015; __AF432137<br>*Streptococcus mitis*; __ATCC__903; __AY281078<br>*Streptococcus parasanguinis*<br>*Streptococcus sanguinis*; __ChDC__OS38; __AF543290<br>*Streptococcus* sp. oral clone GK051; __AY349413<br>*Streptococcus* sp. oral clone P4PA 30 P4; __AY207064<br>*Streptococcus mitis*; __ATCC__15914; __AY281076<br>*Streptococcus* sp. oral strain 12F; __AY134908 |
| ⑲ |  | *Gemella* sp. oral strain A31SC; __AY005050 |
| ⑳ |  | *Prevotella veroralis*<br>*Prevotella* sp. oral clone DO022; __AF385519 |

What is claimed is:

1. A method for analyzing a bacterial community comprising:

amplifying DNAs extracted from a bacterial community by PCR using 16S rRNA genes as templates and fluorescently labeled primers;

cleaving the amplification products with a restriction enzyme to thereby obtain sample PCR fragments;

electrophoresing the sample PCR fragments together with size standard PCR fragments; and comparing the mobilities thereof to thereby determine the sizes of the sample PCR fragments, wherein PCR fragments prepared by using, as a template, a 16S rRNA gene derived from a bacterium contained in the bacterial community to be analyzed are used as the size standards.

2. The method according to claim 1, wherein the determination of the sizes of the sample PCR fragments is carried out with reference to the molecular weights of the size standard PCR fragments.

3. The method according to claim 2, wherein the DNAs are amplified with a pair of primers, wherein the primers are fluorescently labeled in the 5' terminal and 3'-terminal with different colors, respectively.

4. The method according to claim 1, wherein the DNAs are amplified with a pair of primers, wherein the primers are fluorescently labeled in the 5' terminal and 3'-terminal with different colors, respectively.

5. A method for analyzing a bacterial community comprising the following a) to d):

a) extracting DNAs from a bacterial community, amplifying the DNAs by PCR using 16S rRNA genes as templates and fluorescently labeled primers, and cleaving the amplification products with a restriction enzyme to thereby prepare sample PCR fragments;

b) preparing a fluorescently labeled PCR fragment by PCR amplification using, as a template, a 16S rRNA gene derived from a bacterium contained in the bacterial community to be analyzed, and cleaving the amplification product with a restriction enzyme to thereby prepare size standard PCR fragments;

c) simultaneously electrophoresing the size standard PCR fragments and the sample PCR fragments, and comparing the mobilities thereof to thereby determine the sizes of the sample PCR fragments with reference to the molecular weights of the size standard PCR fragments; and d) comparing the sizes obtained at c) with sizes in a database to thereby identify bacterial species.

6. A method for analyzing an oral bacterial flora comprising:

amplifying DNAs extracted from an oral bacterial community by PCR using 16S rRNA genes as templates and fluorescently labeled primers;

cleaving the amplification products with a restriction enzyme to thereby obtain sample PCR fragments;

electrophoresing the sample PCR fragments together with size standard PCR fragments; and comparing the mobilities thereof to thereby determine the sizes of the sample PCR fragments, wherein PCR fragments prepared by using, as a template, a 16S rRNA gene derived from an oral bacterium are used as the size standards.

7. The method according to claim 6, wherein the size standards are PCR fragments prepared by using, as a template, a 16S rRNA gene derived from *Porphyromonas gingivalis*.

8. A method for analyzing an oral bacterial flora comprising the following a) to d):

a) extracting DNAs from an oral bacterial community, amplifying the DNAs by PCR using 16S rRNA genes as templates and fluorescently labeled primers, and cleaving the amplification products with a restriction enzyme to thereby prepare sample PCR fragments;

b) preparing a fluorescently labeled PCR fragment by PCR amplification using, as a template, a 16S rRNA gene derived from an oral bacterium, and cleaving the amplification product with a restriction enzyme to thereby prepare size standard PCR fragments;

c) simultaneously electrophoresing the size standard PCR fragments and the sample PCR fragments, and comparing the mobilities thereof to thereby determine the sizes of the sample PCR fragments with reference to the molecular weights of the size standard PCR fragments; and d) comparing the sizes obtained at c) with sizes in a database to thereby identify bacterial species.

9. The method according to claim 8, wherein the size standards are PCR fragments prepared by using, as a template, a 16S rRNA gene derived from *Porphyromonas gingivalis*.

* * * * *

```
                          SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
gagagtttga tyctggctca g                                        21

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
gaaggaggtg wtccarccgc a                                        21

<210> SEQ ID NO 3
<211> LENGTH: 20
<212> TYPE: DNA
<213> ORGANISM: Artificial Sequence
<220> FEATURE:
```

```
<223> OTHER INFORMATION: Synthetic Oligonucleotide

<400> SEQUENCE: 3
cgcatgccta tcttacagct                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
agttccccta cccatcgtcg                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
cctcactgct gcctcccgta                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
taggactgtc ttccttcacg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
cggtacattc aatgcaatac                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
ctcgcatcct ccgtattacc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tcaccgctga cttaccgaac                                               20
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
ctgccgccac tgaactcaag                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
aagctgcctt cgcaatcgga                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
gctttcgctg tggaagcttg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
ccgtcwattc mtttgagttt                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
gtaaggttcc tcgcgtatca                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
agagtttgat ymtggctcag                                              20

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 16
ggactaccrg ggtatctaa                                                19

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
gtaaggttcc tcgcgtatca                                               20

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
gaataacggg cgatacgag                                                19

<210> SEQ ID NO 19
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 19
caatgggcga gagcctgaa                                                19

<210> SEQ ID NO 20
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 20
acactggtac tgagacacg                                                19

<210> SEQ ID NO 21
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 21
tcccattagc ttgttggtg                                                19

<210> SEQ ID NO 22
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 22
acggactaaa accgcatac                                                19

<210> SEQ ID NO 23
<211> LENGTH: 19
```

-continued

```
<212> TYPE: DNA
<213> ORGANISM: Artificial Sequence
<220> FEATURE:
<223> OTHER INFORMATION: Synthetic Oligonucleotide

<400> SEQUENCE: 23
agcttgctaa ggttgatgg                                                19

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
tctttgacag agtatatgtc                                               20
```